United States Patent
Walter et al.

(10) Patent No.: US 9,895,231 B2
(45) Date of Patent: *Feb. 20, 2018

(54) NECK SPARING TOTAL HIP IMPLANT SYSTEM

(71) Applicant: Concept, Design and Development, LLC, Chagrin Falls, OH (US)

(72) Inventors: Bradley Walter, Thomasville, GA (US); Declan Brazil, Chatswood (AU); Timothy McTighe, Chagrin Falls, OH (US)

(73) Assignee: Concept, Design and Development, LLC, Chagrin Falls, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,977

(22) Filed: Jun. 25, 2013

(65) Prior Publication Data
US 2014/0012392 A1 Jan. 9, 2014

Related U.S. Application Data

(63) Continuation of application No. 12/978,395, filed on Dec. 23, 2010, now Pat. No. 8,470,049, which is a
(Continued)

(51) Int. Cl.
*A61F 2/36* (2006.01)
*A61B 17/16* (2006.01)
(Continued)

(52) U.S. Cl.
CPC .......... *A61F 2/3609* (2013.01); *A61F 2/3601* (2013.01); *A61F 2/3662* (2013.01);
(Continued)

(58) Field of Classification Search
USPC ......... 623/22.11, 23.11, 23.15, 23.18, 23.21, 623/23.24, 23.3, 23.32, 23.33, 23.35,
(Continued)

(56) References Cited

U.S. PATENT DOCUMENTS

2002/0107520 A1* 8/2002 Hoffman .................. 606/72
2006/0184249 A1* 8/2006 Tarabishy ................ 623/23.4
(Continued)

*Primary Examiner* — David Isabella
*Assistant Examiner* — Christine Nelson
(74) *Attorney, Agent, or Firm* — Morriss O'Bryant; Compagni Cannon, PLLC

(57) ABSTRACT

A femoral prosthesis. The femoral prosthesis includes an implant body having a proximal end and a distal end and a shoulder at the proximal end, the shoulder being structured and dimensioned for a tight press fit into the neck of a femur. The implant body includes a trunk at the distal end, the trunk having a wedge formed by a tapered portion extending in the direction of the distal end of the implant, body. The implant, body also includes a medial column extending from the shoulder toward the distal end and a lateral column extending from the shoulder toward the distal end. The wedge, the medial column, and the lateral column to provide multiplanar stability for the implant body and surface area for fixation of the implant body.

16 Claims, 16 Drawing Sheets

Related U.S. Application Data continuation-in-part of application No. 12/874,132, filed on Sep. 1, 2010, now abandoned.

(60) Provisional application No. 61/238,898, filed on Sep. 1, 2009.

(51) Int. Cl.
*A61B 17/17* (2006.01)
*A61F 2/30* (2006.01)

(52) U.S. Cl.
CPC ......... *A61B 17/1668* (2013.01); *A61B 17/175* (2013.01); *A61F 2002/30205* (2013.01); *A61F 2002/30321* (2013.01); *A61F 2002/30334* (2013.01); *A61F 2002/30841* (2013.01); *A61F 2002/30904* (2013.01); *A61F 2002/365* (2013.01); *A61F 2002/368* (2013.01); *A61F 2002/3652* (2013.01); *A61F 2002/3668* (2013.01)

(58) Field of Classification Search
USPC ...................................... 623/23.44
See application file for complete search history.

(56) References Cited

U.S. PATENT DOCUMENTS

2006/0206212 A1\* 9/2006 Zweymuller ............. 623/23.35
2008/0027559 A1\* 1/2008 Crowninshield et al. . 623/23.44

\* cited by examiner

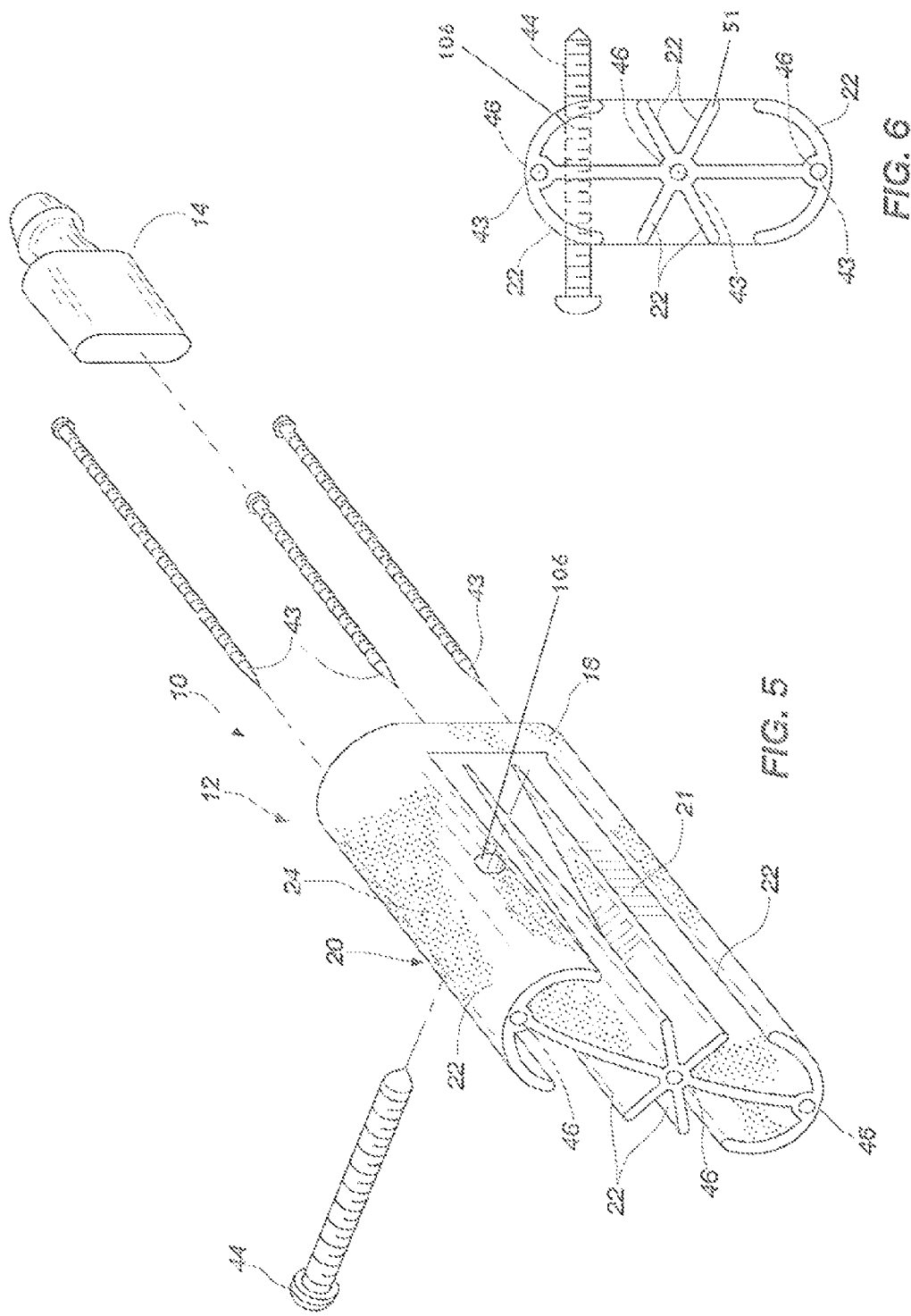

NECK SPARING TOTAL HIP IMPLANT SYSTEM

CROSS-REFERENCE TO RELATED APPLICATIONS

This application is a continuation of U.S. patent application Ser. No. 12/978,395, filed Dec. 23, 2010, which is a continuation-in-part of U.S. patent application Ser. No. 12/874,132, filed Sep. 1, 2010, which claims the benefit of U.S. Provisional Application No. 61/238,898, filed Sep. 1, 2009, entitled FEMORAL PROSTHESIS, which are both hereby incorporated by this reference herein in their entireties, including but not limited to those portions that specifically appear hereinafter, the incorporation by reference being made with the following exception: In the event that any portion of the above-referenced provisional applications is inconsistent with this application, this application supercedes said portion of said above-referenced provisional applications.

STATEMENT REGARDING FEDERALLY SPONSORED RESEARCH OR DEVELOPMENT

Not Applicable.

BACKGROUND

1. The Field of the Present Disclosure

The present disclosure relates generally to an orthopedic implant, for use in a total hip arthroplasty, i.e., a total hip replacement. More specifically, the disclosure relates to a femoral component of a total hip implant, and more particularly, but not necessarily entirely, to a femoral neck sparing implant that may be placed or located in a proximal femur.

2. Description of Related Art

This invention relates in general to prosthesis, parts thereof, or aids and accessories therefor. More particularly, the invention relates to a femoral prosthesis.

Total hip replacement has become the standard of care treatment to address a variety of degenerative and traumatic processes of the nip joint.

Much has been learned and developed over the last several decades of practice and research. Previously, much bone resection and marrow excavation has been necessary to accomplish implant longevity and stability. As time has proceeded, more tissue and bone sparing surgical techniques have been developed. These techniques in general are to facilitate less bone loss in future revision surgeries and to decrease soft tissue injury. Bone is lost from both stress shielding and osteolysis. The problem of bone loss from osteolysis has largely been solved by improvement in the wear properties of modern bearing surfaces. Stress shielding bone loss has been improved by loading the proximal femur with tapered stem geometries or surface replacement devices. Surface replacement devices have a multitude of limitations. First, the procedure can require relatively large exposure and therefore can hardly be called tissue sparing, although bone sparing. Second, the compromised bone of the femoral head is often a poor foundation and can cause early or late failure from collapse. Lastly, femoral neck fracture can occur.

Previous devices have relied on entry into the femoral canal either in a straight entry or in a curvilinear fashion. Some have considered the proximal femoral metaphyseal bone incapable of sustaining load.

Modern minimally invasive surgery, in particular, the "anterior supine muscle sparing" approach, is made more difficult by the straight diaphyseal engaging stems. Shorter curved tapered stems have been made with some improvement in the ease of implantation. However, femoral insertion can still be very challenging.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 5 is an enlarged perspective view of another femoral prosthesis.

FIG. 6 is an end view of the femoral prosthesis shown in FIG. 5.

DETAILED DESCRIPTION

Figures 1, 2A:
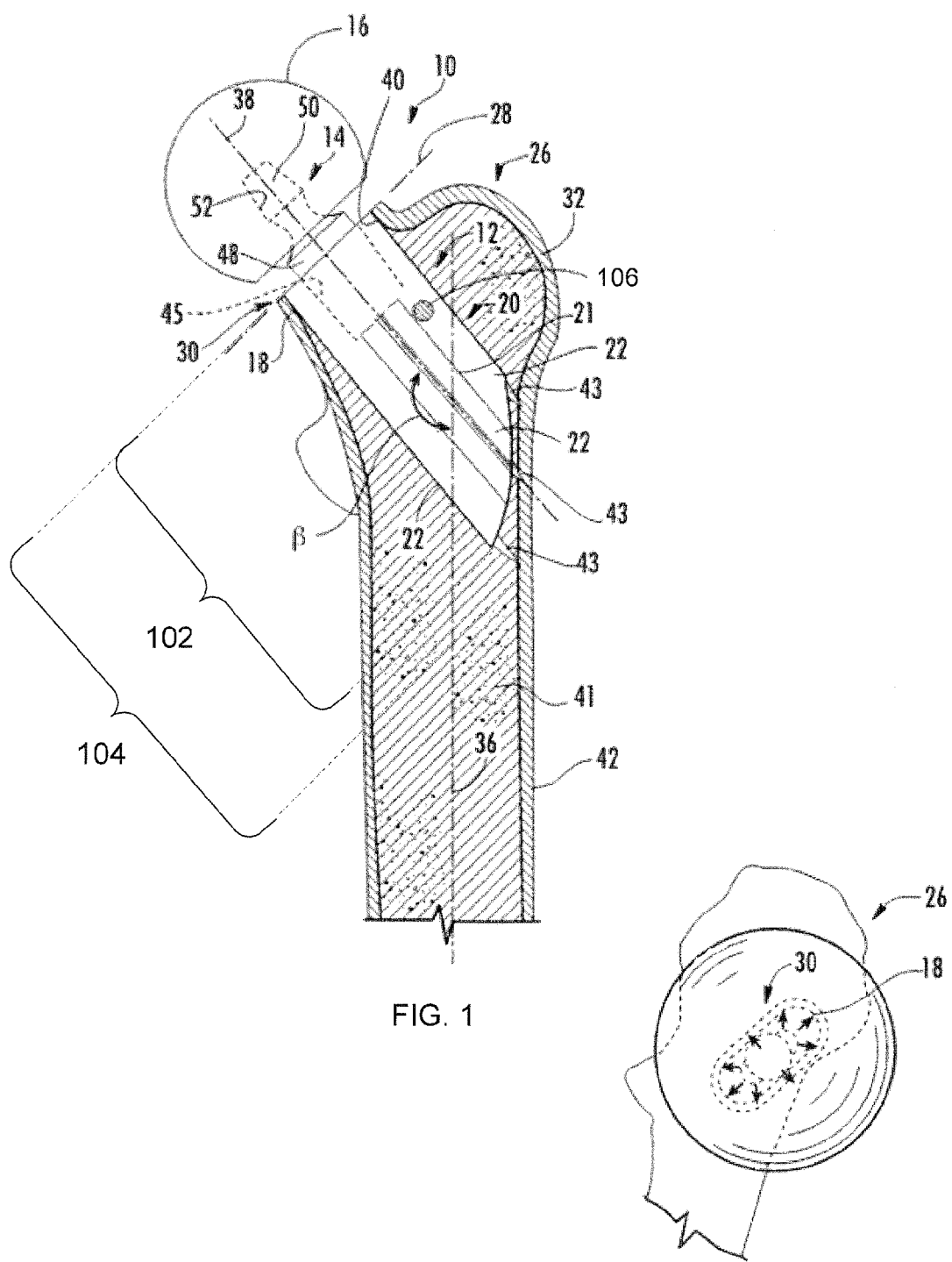
FIG. 1 is a partial sectional view in elevation of the proximal end of a femur and a femoral prosthesis.
FIG. 2A is a diagrammatic partial plan view of the femur and prosthesis shown in FIG. 1, showing hoop stress at the femoral neck.
Figure 2B:
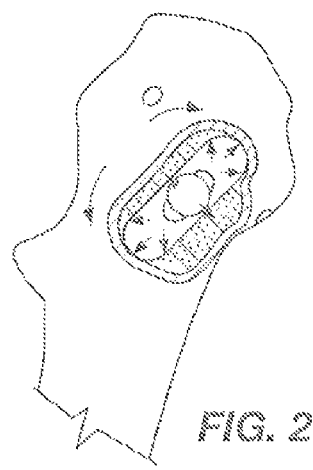
FIGS. 2B-2C are diagrammatic partial plan views of other femurs and the prosthesis, showing hoop stress at the femoral necks.
Figure 2C:
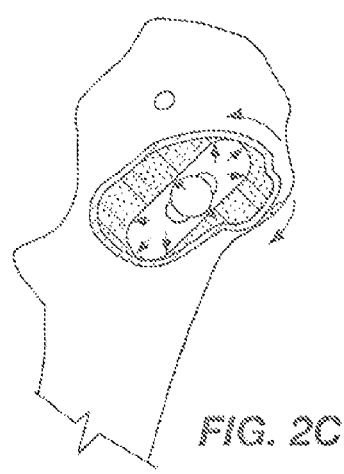

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

Any publications and other reference materials referred to herein to describe the background of the disclosure, and to provide additional detail regarding its practice, are hereby incorporated by reference herein in their entireties, with the following exception: In the event that any portion of said reference materials is inconsistent with this application, this application supercedes said reference materials. Reference materials discussed herein are provided solely for their disclosure prior to the filing date of the present application. Nothing herein is to be construed, as a suggestion or admission that, the inventors are not entitled to antedate such disclosure by virtue of prior disclosure, or to distinguish the present disclosure from the subject matter disclosed in the reference materials.

It must be noted that, as used in this specification and the appended claims, the singular forms "a," "an," and "the" include plural referents unless the context clearly dictates otherwise.

In describing and claiming the present disclosure, the following terminology will be used, in accordance with the definitions set out below.

As used herein, the terms "comprising," "including," "containing," "characterized by," and grammatical equivalents thereof are inclusive or open-ended terms that do not exclude additional, unreel ted elements or method steps.

As used herein, the term "proximal" is a relative term and shall refer broadly to the concept of a more near portion. For example, the neck is the proximal-most portion of the prosthesis, relative to other portions of the prosthesis, because it is the nearest portion when said prosthesis is installed. When referring to a portion of the human body or a device or structure attached to the human body, the term "proximal" is a relative term and shall refer broadly to the concept of a portion closer to the center of the body.

As used herein, the term "distal" shall generally refer to the opposite of proximal, and thus to the concept of a further portion, a furthest portion, or a portion more distant from the center of the body, depending upon the context.

As used herein, the phrase "in an at least partially proximal-to-distal direction" shall refer generally to a two-dimensional concept of direction in which the "proximal-to-distal" direction defines one direction or dimension. An item that extends in a non-parallel direction with respect to the "proximal-to-distal" direction, that is, at a non-straight angle thereto, thereby involves two components of direction, one of which is in the "proximal-to-distal" direction and the other being in a direction orthogonal to the "proximal-to-distal" direction. For example, the medial column extends in a proximal-to-distal direction.

It will be appreciated that the structure and apparatus disclosed herein is merely one example of a means for a femoral prosthesis, and it should be appreciated that any structure, apparatus or system for femoral prosthesis which performs functions the same as, or equivalent to, those disclosed herein are intended to fall within the scope of a means for a femoral prosthesis, including those structures, apparatus or systems for a femoral prosthesis which are presently known, or which may become available in the future. Anything which functions the same as, or equivalently to, a means for a femoral prosthesis falls within the scope of this element.

Referring now to the drawings, there is illustrated in the FIGS. 1-4 one embodiment of a femoral prosthesis 10 generally comprising an implant body 12 supporting a neck 14, which may be without modularity or optionally a modular neck. The neck 14 may have a Morse taper, as is known in the art, to accommodate a substantially spherical joint ball, bearing or prosthetic head 16 at the proximal end of the neck 14. The design may accommodate a wide variety of spherical ball sizes and/or materials (e.g., metal or ceramic).

Close below this prosthetic head 16, the implant body 12 may be provided with a shoulder 18 at its proximal end. This shoulder 18 may be conical or tapered at an angle. The angle may be in a range between about 2 degrees and about 10 degrees, or some other suitable angle that creates a Morse tapered or other machine taper retentive effect in the neck of the femur 26, as will become apparent in the description that follows. The shoulder 18 may be structured, and dimensioned for a tight press fit into the femoral neck 30, and thus increase hoop stress at the neck 30 (i.e., depicted by the radially directed arrows in FIGS. 2A-2C). The shoulder 18 may have a fixation surface, which may be rough and porous to promote impaction and/or press-fit of the shoulder 18 into the femoral neck 30 and subsequent fixation (e.g., ingrowth or ongrowth) of the cortical bone of the femoral neck 30 into shoulder 18.

As shown in FIG. 3, FIGS. 5-7 include a trunk 20. The trunk 20 of the embodiment shown in FIGS. 5-7 includes an alternative arrangement of fins 22, as shown.

Figure 8A:
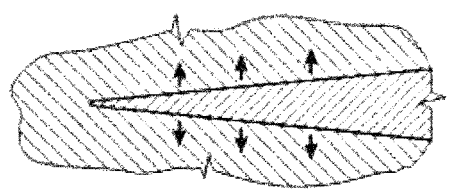
FIGS. 8A-8B are sectional views of prosthesis.
Figure 8B:
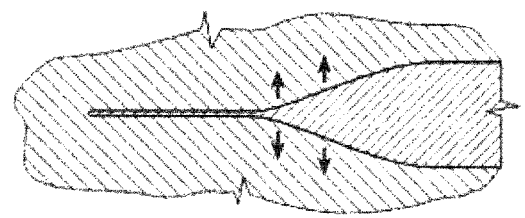

Immediately below the shoulder 18, the implant body 12 merges into a trunk 20. The trunk 20 may have a generally sharply tapered portion extending from the shoulder 18 in the direction of the distal end of the trunk 20 to form a wedge 21, as shown for example in FIG. 8A, or a knife edge, as shown for example in FIG. 8B. The trunk 20 may be provided with longitudinally extending webs or fins 22. The fins 22 may function to provide a large surface area for initial multi-planar stability and an increased surface area for long term fixation (e.g., bony ingrowth or ongrowth), as will become apparent in the description that follows. Although other fin configurations may be suitable, the illustrated implant body 12 has one or more superior (i.e., higher) fins and one or more inferior (i.e., lower) fins. One or more central fins may also be provided. The fins 22 may provide increased surface area contact or maximize surface area contact in the metaphyseal bone for fixation (e.g., bony ingrowth or ongrowth) and initial or preliminary cancellous bone press fit stability or fixation. The implant body 12 (e.g., the shoulder 18 and trunk 20) may be porous to provide long term stability from bony ingrowth or ongrowth. The wedge 21 of the trunk 21 may facilitate dilation and impaction of the cancellous bone. This may prevent the need for removal of substantial cancellous bone.

Figure 3:
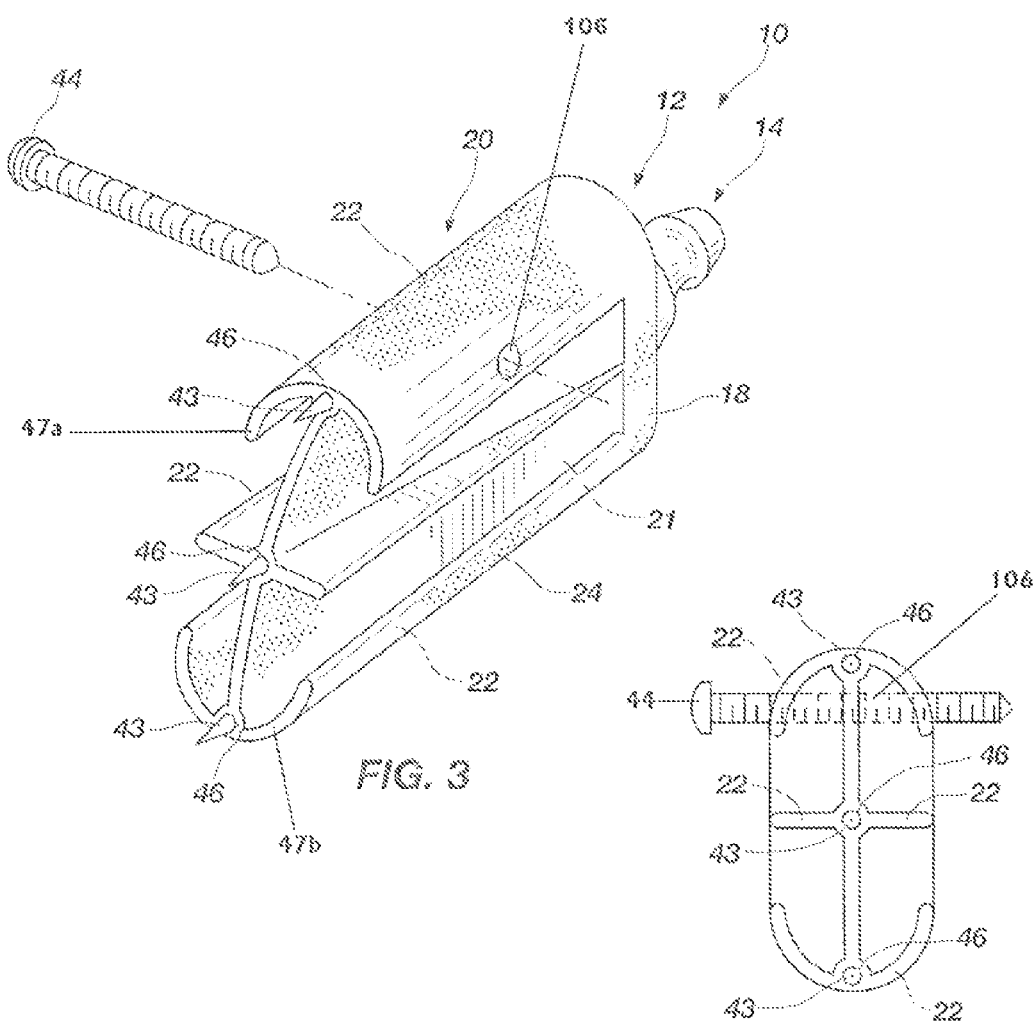
FIG. 3 is an enlarged perspective view of a femoral prosthesis.
Figure 4:
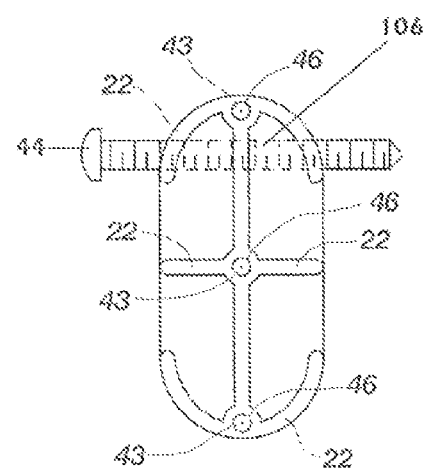
FIG. 4 is an end view of the femoral prosthesis shown in FIG. 3.
Figure 7:
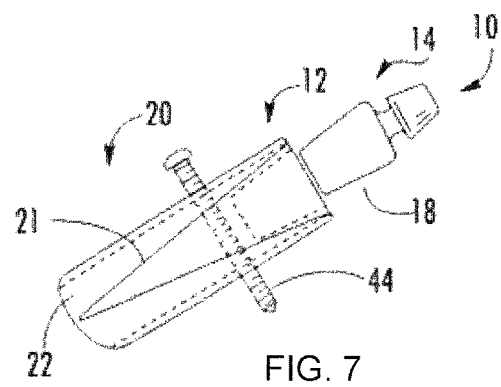
FIG. 7 is an exploded sectional view of the prosthesis shown in FIG. 5.

As can be perhaps best observed in FIG. 3, terminal ends 47a and 47b of the medial and lateral ones of the fins 22 may be C-shaped. Thus, it will be understood that a cross-section of the medial and lateral ones of the fins 22 may be C-shaped. Also, as can be observed in FIG. 3, the central ones of the fins 22 may extend perpendicularly from the wedge 21. As perhaps best observed in FIGS. 5 and 6, a terminal end 51 of the central ones of the fins 22 may be X-shaped. Thus, it will be understood that a cross-section of the central ones of the fins 22 may be X-shaped.

The shoulder 18 may be shaped and dimensioned to approximate the shape and dimension of the femoral neck to further maximize surface area contact. The implant body 12 may have an overall elongated lateral cross-section, or a cross-section that otherwise fits the anatomy of the femoral neck to reduce rotation, and may have a substantially straight long axis so the implant body 12 does not curve into the diaphysis of the femur. To this end, the superior and inferior fins 22 may be curved to approximate the geometry of the superior and inferior part of the neck 18 (see FIGS. 2A-2C). These curves may be substantially the same geometry as the corresponding curved portions of the femoral neck. The implant body 12 and neck 14 may be metal. The metal used may be titanium, chrome-cobalt or stainless steel based, or any metal commonly used in hip prosthesis construction.

The implant body 12 may be porous, and may have a porous coating, layer or surface 24. An example of such a coating is titanium plasma spray, which promotes bony ingrowth or ongrowth into prosthetic implants. The coating may further be in the form of sintered beads, plasma spray, a hydroxyapatite (HA), trabecular metal, porous titanium, or another suitable form, depending on the type of metal used for the prosthesis 10, as the prosthesis may be entirely formed from the same material (e.g., titanium, ail chrome cobalt, or other suitable material).

It should be appreciated that the implant body 12 of the prosthesis 10 may be available in various sizes depending on anatomical requirements, and as mentioned above, the prosthetic head 16 may be a modular head, or a non-modular head.

Fixation of the prosthesis 10 to the femur can be achieved by inserting the implant body 12 into the open neck of a femur, along the anatomic or longitudinal axis of the femoral neck, as set forth for example in the description that follows. Because the implant body 12 is straight and oriented along the longitudinal axis of the femoral neck 30, rotational alignment, can be allowed to shift based on anatomical variations.

In FIG. 1, there is illustrated femur 26 with an osteotomy or cut extending along a plane 28 perpendicular to the longitudinal axis of the femoral neck 30.

The implant body 12 may be fitted into the femoral neck 30 at an angle β to the longitudinal axis 36 of the femur 26 so that the long axis 38 of the implant body 12 corresponds approximately to the axis of a healthy femoral neck. That is to say, the implant body 12 may be inserted from the proximal direction into the femoral neck 30 so that the long axis 38 of the implant body 12 coincides with the axis made in the preoperative femur by an imaginary line connecting the center of the femoral neck 30 with the center of the femoral head, or at an angle β approximately corresponding to the normal anatomy of the patient (usually between 120 and 150 degrees), and preferably the cervico-diaphyseal angle (i.e., the angle between the long axis of the femoral neck and the longitudinal axis 36 of the femur 26), which varies per individual.

In some embodiments, the implant body 12 may contact the inner cortical lateral wall 40 of the femoral neck 30 by tightly fitting the implant body 12 into the femoral neck 30. In another embodiment, the implant body 12 does not contact the inner cortical lateral wall 40. The implant body 12 may have an overall length 102. The implant body 12 may be sized such that the overall length 102 causes the distal end of the implant body 12 to extend between sixty (60) percent and eighty (80) percent of a distance 104 from a resection of the femoral neck 28 to the inner cortical lateral wall 40.

The tapered shoulder 18 at the proximal end of the implant body 12, when inserted in the neck 30 of the femur 26, may form a tight press fit within the neck 30 of the femur 26 to provide optimum contact and load transfer between the engagement surfaces of the shoulder 18 of the implant body 12 and the neck 30 of the femur 26. The tight press fit configuration may increase the hoop stress at the neck 30 of the femur 26 (as represented by the arrows in FIGS. 2A-2C), and thus increase the retentive effect of the shoulder 18 in the neck 30 of the femur 26. It should be appreciated that the shape of the implant body 12 may differ from that of the femoral neck 30 (e.g., due to anatomic variations). The implant body 12 may simply wedge into the "hoop" formed by the femoral neck 30 and thus increase hoop stress. It should be appreciated that the shape of the implant body 12 could be custom made to each patient, for example, using magnetic resonance imaging (MRI) or computer tomography (CT) templating, as mentioned below.

The surfaces of the implant body 12 disposed for engaging the interior of the femur 26 are broadly fixation surfaces. The wedge 21 and the longitudinally extending fins 22 of the trunk 20 of the implant body 12 may penetrate the spongiosa 41 inside the femur 26 to secure the implant body 12 in the femur 26. The overall elongated shape of the lateral cross-section of the implant body 12 may hold the implant body 12 securely against movement about the long axis 38 of the implant body 12 after implantation. The wedge 21 and the fins 22 may provide increased surface contact for initial and late fixation. Fixation (e.g., bony ingrowth or ongrowth) may be encouraged on all surfaces of the implant body 12, including shoulder 18, the wedge 21, and the fins 22. It should be appreciated that the shape and highly porous surface of the implant body 12, including the shoulder 18, the wedge 21, and the fins 22, may, in addition to resisting rotational movement, resist movement in all planes.

The distal end of the implant, body 12 may be cut on an angle to the long axis 38 of the implant body 12, so that the distal end is substantially pointed. Moreover, the distal end of the implant body 12, when inserted in the femur 26, may be generally aligned with or parallel to the inner surface of the lateral wall 42 of the femur 26 or along the longitudinal axis 38 of the femur 26. The distal end of the implant body 12 remains within the femur 26, so as to not extend beyond the femur 26. It should be appreciated that the distal end of the implant body 12 may be curved. For example, a curved surface may be superimposed on the angled distal end of the implant body 12, or otherwise curved, such as curved transversely in relation to the long axis 38 of the implant body, to provide clearance between the distal end of the implant body 12 and the inner surface of the lateral wall 42 of the femur 26, as clearly shown in FIG. 1.

It should be appreciated that the prosthesis 10 may be installed and used without requiring any other fastener on the femur 26. The prosthesis does not require screws or other fasteners to be placed in the femur 26, and it does not require any sort of support plate on the lateral wall of the femur 26.

Notwithstanding, one or more optional fasteners 43, such as pins, spikes or screws, may attach the implant body 12 to the lateral wall 42 of the femur 26, or just contact the inner surface of the lateral wall 42 (without penetration), which may add initial stability to the implant body 12. The fasteners 43 may add stability to the construct by giving further stability to the implant body 12 of the prosthesis 10.

A fastener 43, for example, may pass through a tubular channel 46 in the center of the implant body 12 of the prosthesis 10. The head of the center fastener 43 may be located in the base of a female Morse taper 45 or other machine taper in the implant body 12, if a modular neck is used. Additionally, fasteners 43 may also pass through tubular channels 46 in the implant body 12 of the prosthesis 10, flanking the center of the implant body 12, adjacent the superior and inferior fins. The flanking fasteners can be used to the exclusion of the center fasteners and vice versa. For example, if a non-modular neck is used, flanking fasteners may be used to the exclusion of the center fasteners. It should be appreciated that the fasteners 43 may or may not penetrate the lateral wall 42 of the femur 10 to breach the lateral wall 42. The fasteners 43 may function to further reduce the likelihood of movement, of the prosthesis 10 in all planes within the femoral neck 30. The use of fasteners 43 may be dependent, on the bone quality of the patient.

One or more anterior/posterior fasteners 44, such as screws (best shown in FIG. 3) may be provided. These fasteners 44 pass through one or more anterior/posterior cylindrical channels 106 in the implant body 12, and past though and/or threadably engage the anterior/posterior cortex of the femur 26. The fasteners 44 may allow for some load transfer to the anterior and posterior cortex of the femur 26 through the fasteners 44. In the illustrated embodiment, the one or more anterior/posterior channels 106 are circular in cross section. In certain embodiments, the one or more anterior/posterior channels 106 may be elongate in cross section. It should be appreciated, that the prosthesis 10 can be used without cement.

If a modular neck 14 is used, the distal end of the neck 14 may have a male Morse taper 48 or other machine taper that may cooperate with a female Morse taper 45 or other machine taper in the implant body 12 and thus act as a joining portion in connecting the implant body 12 of the prosthesis 10 for the prosthetic head 16. Adjustments in the length of the neck 14 may be accommodated with the provision of necks of varying length. The Morse tapers 46, 48 or other machine tapers may be provided to accommodate a modular neck 14. Such tapers would not be necessary if a non-modular neck is used.

The prosthetic head 16 may engage a male Morse taper 50 or other machine taper provided at the proximal end of the neck 14. The prosthetic head 16 may have a female Morse taper 52 or other machine taper configured to receive the male Morse tapered or other machine tapered conical head 50 at the proximal end of the neck 14, as is well known in the art. Hence, a modular neck 14 may have a Morse taper 48, 50 or other machine taper at each end, and a length of straight section connecting the Morse tapers 48, 50 or other machine tapers. The length of the straight section may vary so that necks of various sizes can be used for patients with differing requirements.

Prosthetic heads may be of various diameters depending on the type of hip arthroplasty (i.e., hip replacement) being performed (e.g., hemiarthoplasy versus total nip arthroplasty), and the type of acetabular component used.

The prosthesis 10 loads the proximal end of the femur 26, and thus prevents bone resorption. Very little bone is resected in the implantation process. Hence, the femoral prosthesis 10 is bone sparing. The prosthesis 10 may maintain its stability on initial implantation with the press fit in the femoral neck 30 via high hoop stress and a large metaphyseal bone surface contact area. This prosthesis may provide long term reliability while simplifying the technique of implantation through an anterior approach. The prosthesis 10 permits ease of insertion via the anterior approach, following the anatomic neck angle. This allows less tissue dissection because there is less need to elevate the femur in order to gain access to the longitudinal axis of the femoral diaphysis.

The prosthesis 10 is ideal for MRI or CT templating in the hip. Using MRI or CT templating, a custom prosthesis as described above may be produced to specifically approximate or match an individual patient's anatomy, thus producing a custom-fit implant body.

Figure 9A:
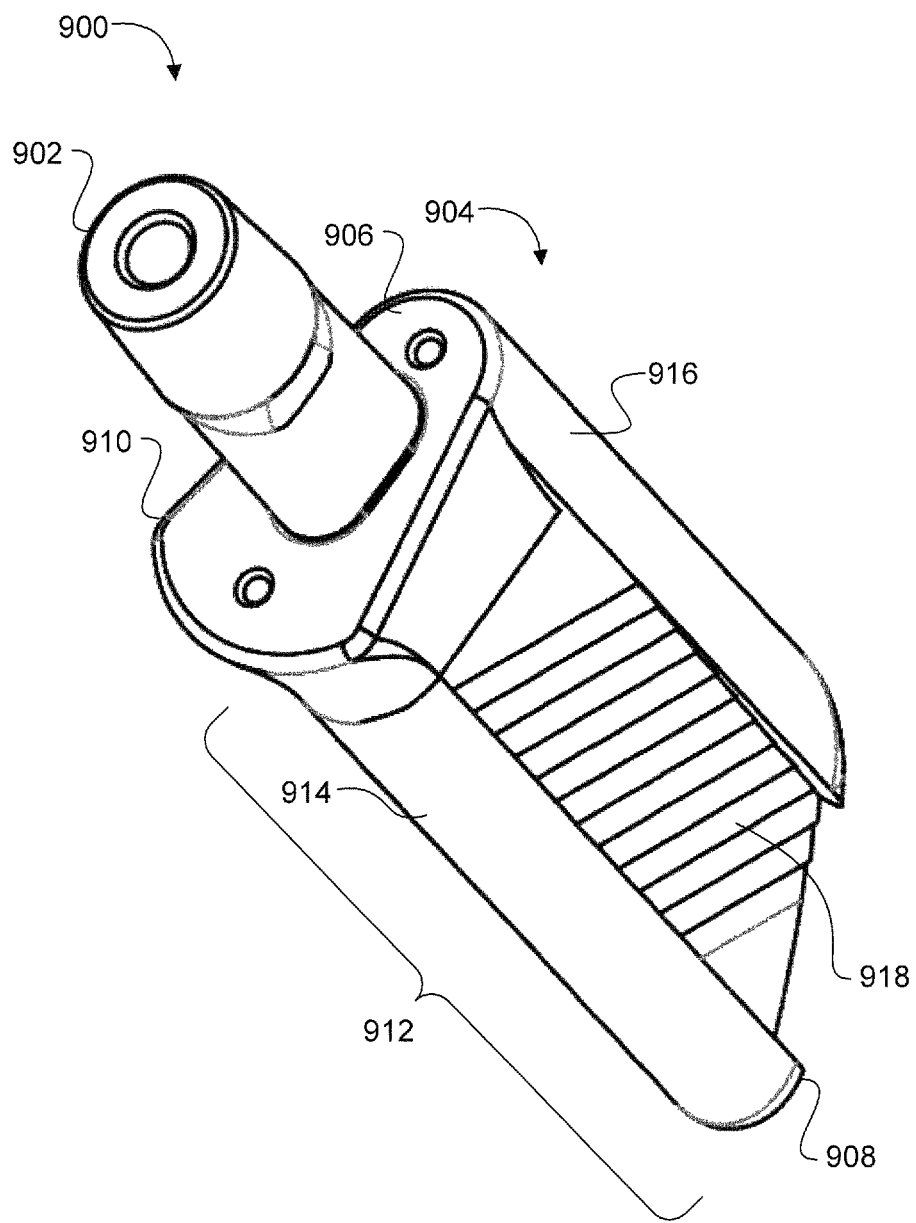
FIG. 9A shows a perspective view of a femoral prosthesis.
Figure 9B:
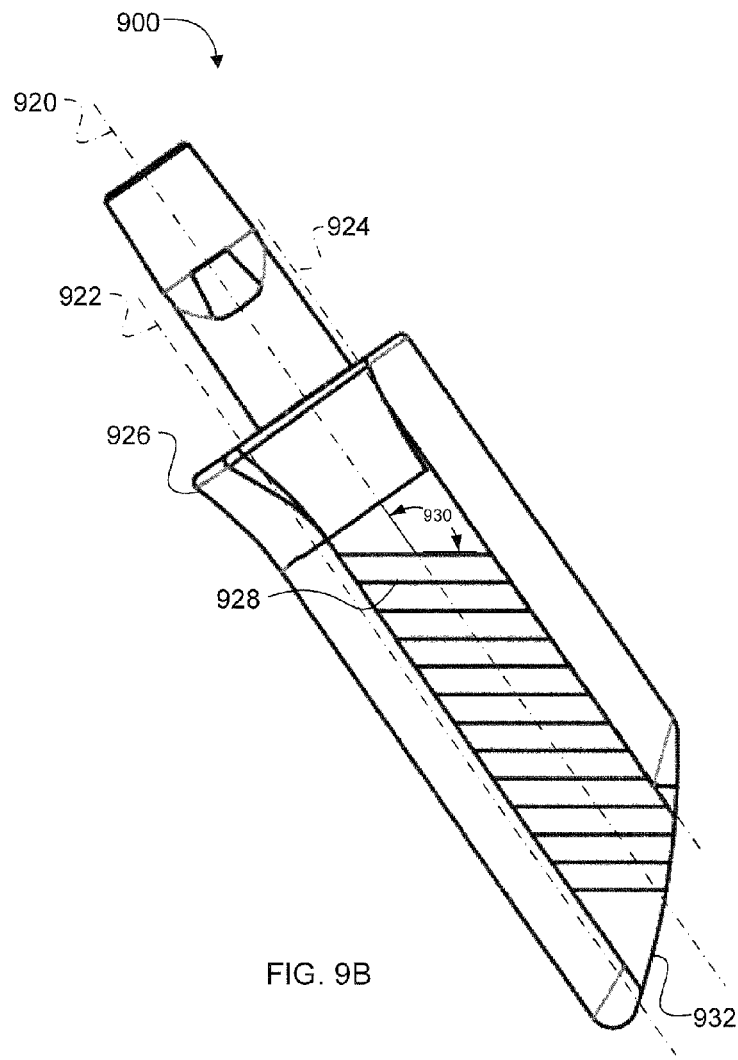
FIG. 9B snows an anterior view of the femoral prosthesis of FIG. 9A.
Figure 9C:
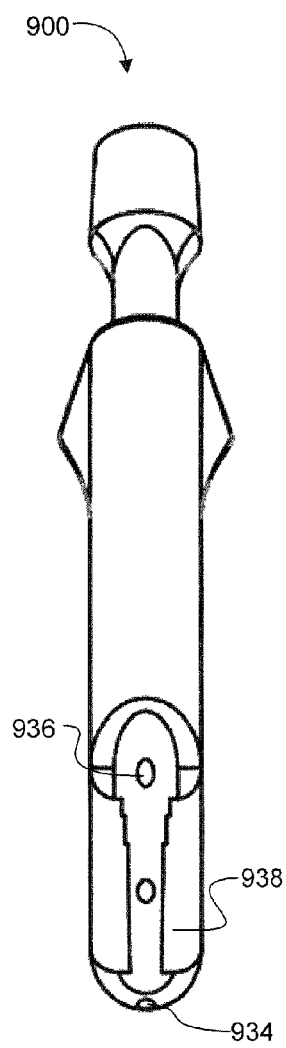
FIG. 9C shows lateral view of the femoral prosthesis of FIG. 9A.

FIGS. 9A-9C illustrate an alternative embodiment of a femoral prosthesis 900. FIG. 9A shows a perspective view of the femoral prosthesis 900. FIG. 9B shows an anterior view of the femoral prosthesis 900. FIG. 9C shows lateral view of the femoral prosthesis 900. The femoral prosthesis 900 includes a neck 902 and an implant body 904. The implant body 904 includes a proximal end 906 and a distal end 908, a shoulder 910 and a trunk 912. The shoulder 910, in some embodiments, located at or near the proximal end 906 of the implant body 904 and is similar to the shoulder 18 described in relation to FIGS. 1-4. The shoulder 910 may constitute an outer perimeter of the implant body 904. The femoral prosthesis 900 is used in a hip replacement.

The trunk 912, in one embodiment, extends from the shoulder 910 toward the distal end 906 of the implant body 904. The trunk 912 includes medial column 914, a lateral column 916, and a connecting body 918 that separates the medial column 914 and the lateral column 916. The connecting body 918 may be connected to the medial column 914 on a medial side of the connecting body 918, and connected to the lateral column 916 on a lateral side of the connecting body 918.

In some embodiments, the connecting body 918 is a wedge and has a cross section that is substantially wedge-shaped. For example, the connecting body may have a cross section similar to that illustrated in FIG. 8A. The connecting body 918 may have a cross section that has a knife edge shape, similar to that illustrated in FIG. 8B.

As best shown in FIG. 9B the implant body 904 has a long axis 920 running through the center of the neck 902 and the length of the implant body 904. The implant body 904, in some embodiments, is substantially straight, and the long axis 920 is substantially straight and in the center of the implant body 904.

The implant body 904 may include a medial column axis 922. The medial column axis 922 runs essentially through the center of the medial column 914. The medial column axis 922 may run through successive center points of the medial column 914. In one embodiment, the medial column 914 has a curved outer surface (best seen in FIG. 13) with a radius and a center point. In some embodiments, the medial column axis 922 runs through the center points. In one embodiment, the medial column axis 922 is substantially parallel to the long axis 920.

The implant body 904 may include a lateral column axis 924. The lateral column axis 924 runs essentially through the center of the lateral column 916. The lateral column axis 924 may run through successive center points of the lateral column 916. In one embodiment, the lateral column 916 has a curved outer surface (best seen in FIG. 13) with a radius and a center point. In some embodiments, the lateral column axis 924 runs through the center points. In one embodiment, the lateral column axis 924 is substantially parallel to the long axis 920. In some embodiments, the medial column axis 922 and the lateral column axis 924 are substantially parallel.

The implant body 904, in some embodiments, includes a flare 926 on a medial side of the shoulder 910 and a proximal portion of the medial column 914. The flare 926 extends radially from the medial column axis 922, becoming larger as the flare 926 progresses along the implant body 904 in a distal to proximal direction. The flare 926 acts to load the calcar region of the resected femur and helps prevent bone resorbtion.

In certain embodiments, the implant body 904 includes one or more terraces 928 on the connecting body 918. The terraces 928 may be arranged such that each terrace 928 undercuts a more proximal level of the connecting body 918. In some embodiments, the connecting body 918 is roughly wedge-shaped, and the slope of the wedge is formed, by successive terraces 928 on the anterior and posterior faces of the connecting body 918. The terraces 928 may provide increased boding and stress offloading of the implant body 904 to the femur.

In some embodiments, the terraces 928 are angled relative to the long axis 920 of the implant body 904 at a terrace angle 930. In certain embodiments, the terrace angle 930 is between 125 degrees and 160 degrees. In one embodiment, the terrace angle 930 is such that the terraces 928 run perpendicular to a long axis of the femur when the implant body 904 is installed in the femur. In an alternate embodiment, the terrace angle 930 is such that the terraces 928 run perpendicular to the long axis 920 of the implant body 904.

The distal end 908 of the implant body 904, in some embodiments, is angled relative to the long axis 920 of the implant body 904. In one embodiment, the distal end 908 is angled such that it is roughly parallel with the inner cortical wall of the femur when the implant body 904 is installed. In some embodiments, the distal end 908 has a curved surface 932 superimposed on the distal end 908. In one embodiment, the curved surface 932 is a transverse curve.

The implant body 904, in some embodiments, includes a medial cannula 934. The medial cannula 934 may run the length of the implant body 904 such that it is accessible at both the proximal end 906 and the distal end 908 of the implant body 904. In one embodiment, the medial cannula 934 runs along the medial column axis 922. The medial cannula 934 provides a pathway for a guide wire to guide the implant body 904 during installation.

In some embodiments, the implant body 904 includes a lateral cannula 936. The lateral cannula 936 may run the length of the implant body 904 such that it is accessible at both the proximal end 906 and the distal end 908 of the implant body 904. In one embodiment, the lateral cannula 936 runs along the lateral column axis 924. The lateral cannula 936 provides a pathway for a guide wire to guide the implant body 904 during installation.

The medial column 914, in one embodiment, has an inside surface 938. The inside surface 938 may be formed by a taper of the connecting body 918 relative to the medial column 914. In one embodiment, the inside surface 938 is substantially flat, or planar. In an alternate embodiment, the inside surface 938 is convex over at least a portion of the inside surface 938. The lateral column 916 may have a corresponding inside surface (not shown) which may also be substantially planar, convex, or another shape over at least a portion of the inside surface of the lateral column 916.

In one embodiment, the medial column 914 and the lateral column 916 have a substantially constant lateral cross sectional area along the trunk 912. In some embodiments, the medial column 914 has a decreasing cross sectional area in the region where the flare 926 is located as cross sections move from the proximal end 906 toward the distal end 908 of the implant body 904.

Figure 10A:
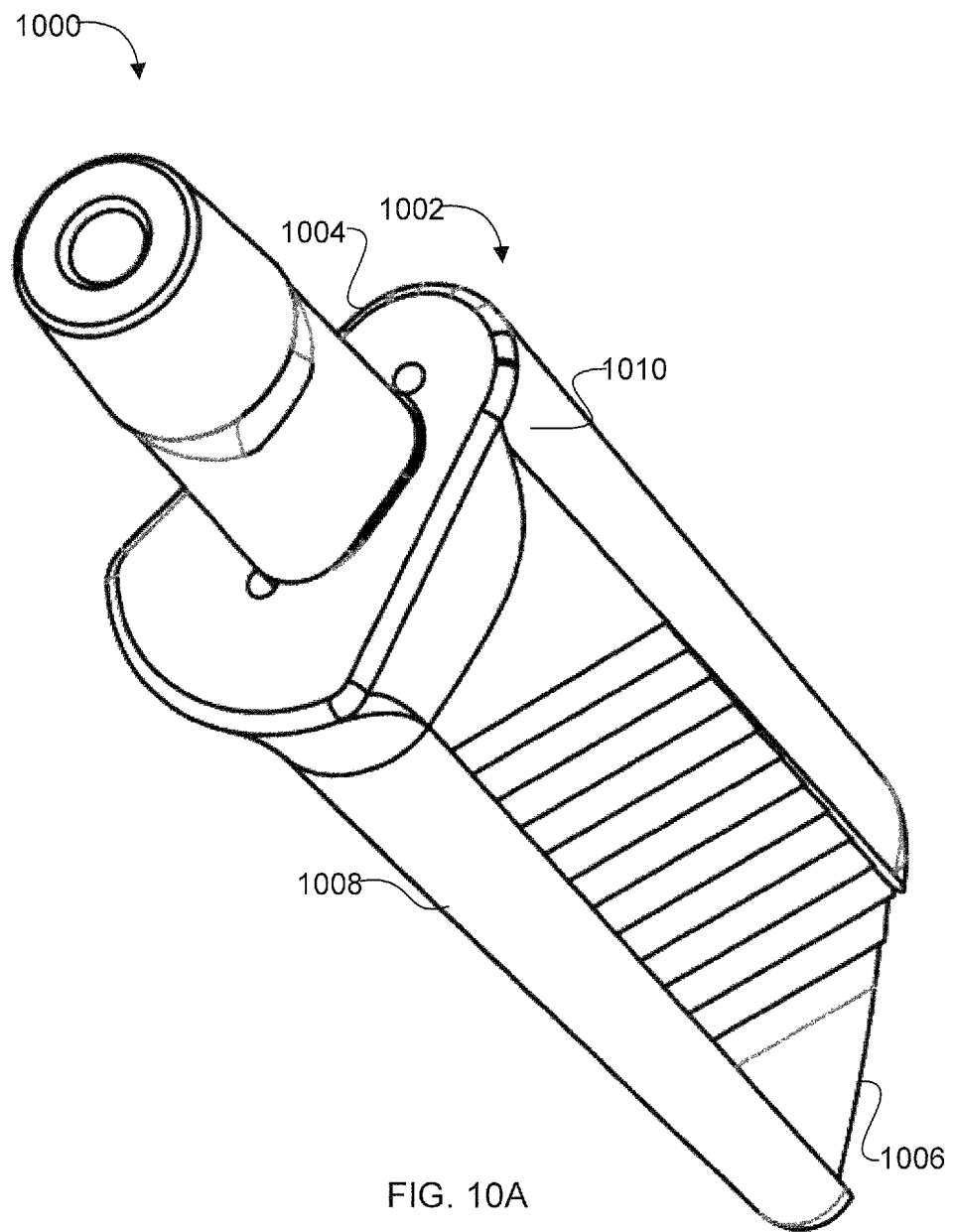
FIG. 10A shows a perspective view of a femoral prosthesis.
Figures 10B, 10C:
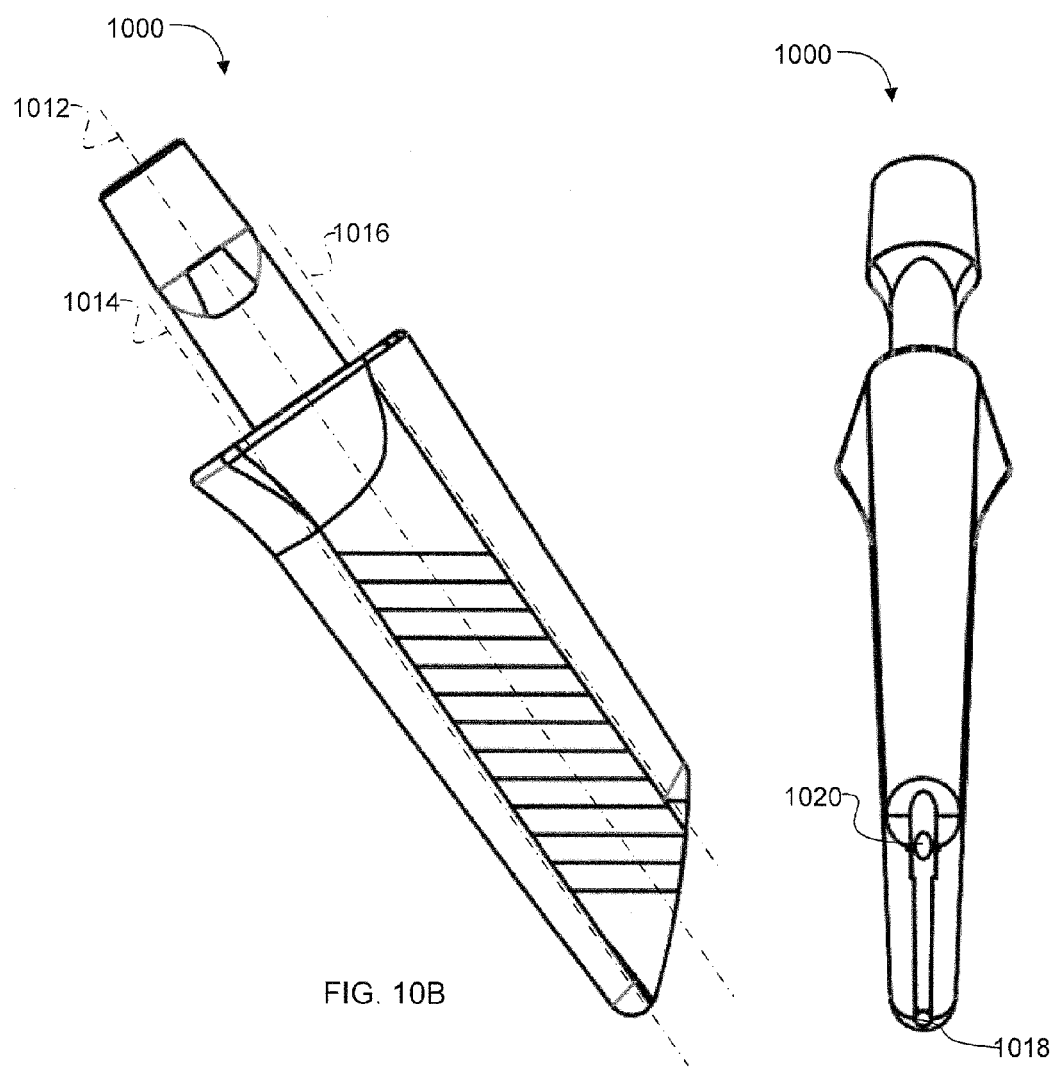
FIG. 10B shows an anterior view of the femoral prosthesis of FIG. 10A.
FIG. 10C shows lateral view of the femoral prosthesis of FIG. 10A.

FIGS. 10A-10C illustrate another embodiment of a femoral prosthesis 1000. FIG. 10A snows a perspective view of the femoral prosthesis 1000. FIG. 10B shows an anterior view of the femoral prosthesis 1000. FIG. 10C shows lateral view of the femoral prosthesis 1000. The femoral prosthesis 1000 includes many structures and features similar to those of the femoral prosthesis 900 described above. The femoral prosthesis 1000 is used in a hip replacement.

In one embodiment, the femoral prosthesis 1000 includes an implant body 1002 with a proximal end 1004, a distal end 1006, a medial column 1008, and a lateral column 1010. The medial column 1008, in one embodiment, tapers along at least a portion of the medial column 1008 from the proximal end 1004 to the distal end 1006. In one embodiment, the cross sectional area of the medial column 1008 decreases along at least a portion of the column as cross sections are viewed in a proximal to distal direction.

The lateral column 1010, in one embodiment, tapers along at least a portion of the lateral column 1010 from the proximal end 1004 to the distal end 1006. In one embodiment, the cross sectional area of the lateral column 1010 decreases along at least a portion of the column as cross sections are viewed in a proximal to distal direction.

In some embodiments, the implant body 1002 includes a long axis 1012 running through the center of the implant body 1002 along its length. The implant body 1002, in some embodiments, is substantially straight, and the long axis 1012 is substantially straight and in the center of the implant body 1002.

The implant body 1002 may include a medial column axis 1014. The medial column axis 1014 runs essentially through the center of the medial column 1008. The medial column axis 1014 may run through successive center points of the medial column 1008. In one embodiment, the medial column 1008 has a curved outer surface (best seen in FIG. 13) with a radius and a center point. In some embodiments, the medial column axis 1014 runs through the center points. In one embodiment, the medial column axis 1014 is substantially parallel to the long axis 1012.

The implant body 1002 may include a lateral column axis 1016. The lateral column axis 1016 runs essentially through the center of the lateral column 1010. The lateral column axis 1016 may run through successive center points of the lateral column 1010. In one embodiment, the lateral column 1010 has a curved outer surface (best seen in FIG. 13) with a radius and a center point. In some embodiments, the lateral column axis 1016 runs through the center points. In one embodiment, the lateral column axis 1016 is substantially parallel to the long axis 1012. In some embodiments, the medial column axis 1014 and the lateral column axis 1016 are substantially parallel.

The implant body 1002, in some embodiments, includes a medial cannula 1018. The medial cannula 1018 may run the length of the implant body 1002 such that it is accessible at both the proximal end 1004 and the distal end 1006 of the implant body 1002. In one embodiment, the medial cannula 1018 runs along the medial column axis 1014. The medial cannula 1018 provides a pathway for a guide wire to guide the implant body 1002 during installation.

In some embodiments, the implant body 1002 includes a lateral cannula 1020. The lateral cannula 1020 may run the length of the implant body 1002 such that it is accessible at both the proximal end 1004 and the distal end 1006 of the implant body 1002. In one embodiment, the lateral cannula 1020 runs along the lateral column axis 1016. The lateral cannula 1020 provides a pathway for a guide wire to guide the implant body 1002 during installation.

Figure 11A:
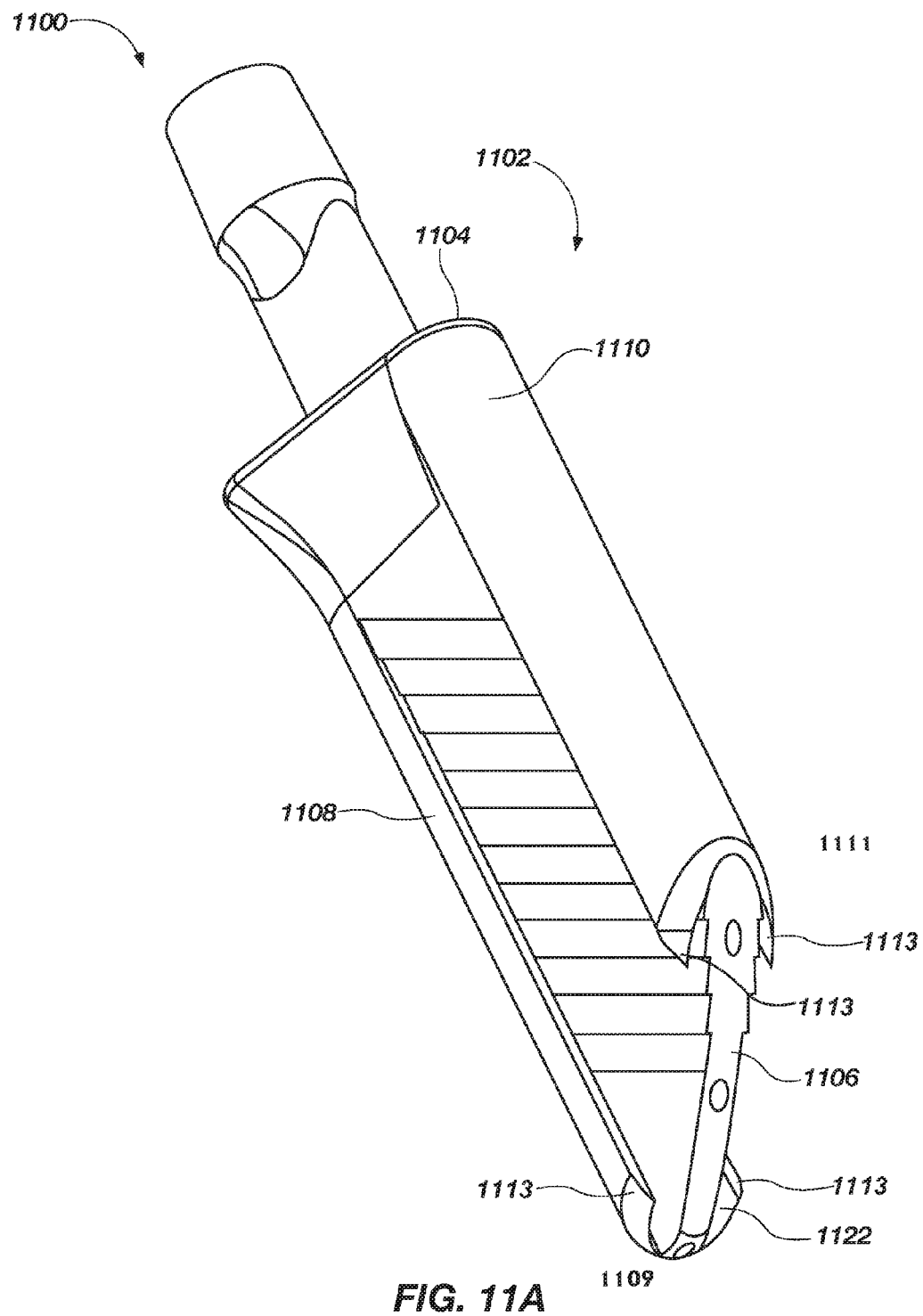
FIG. 11A shows a perspective view of a femoral prosthesis.
Figures 11B, 11C:
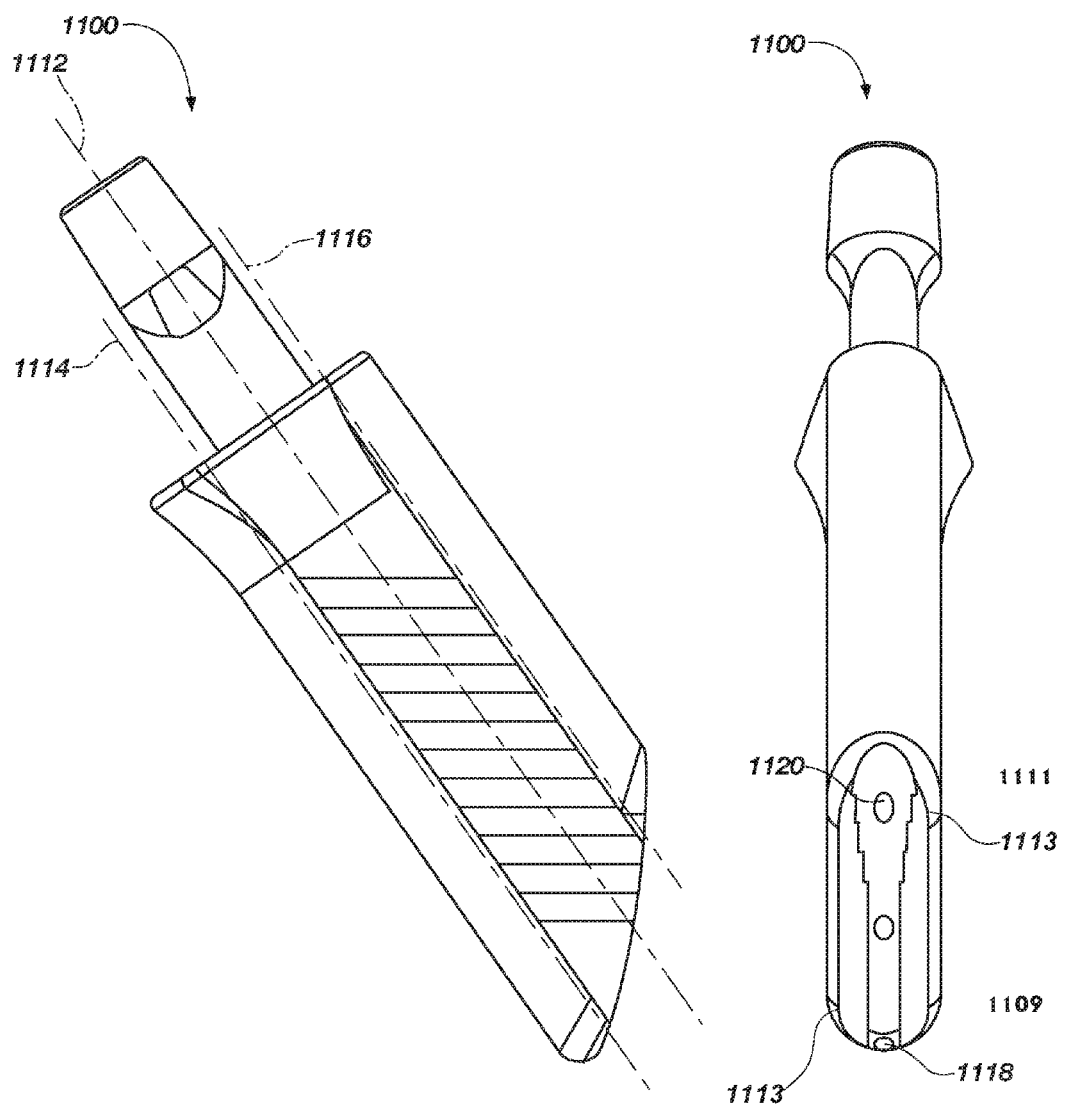
FIG. 11B shows an anterior view of the femoral prosthesis of FIG. 11A.
FIG. 11C shows lateral view of the femoral prosthesis of FIG. 11A.

FIGS. 11A-11C illustrate another embodiment of a femoral prosthesis 1100. FIG. 11A shows a perspective view of the femoral prosthesis 1100. FIG. 11B shows an anterior view of the femoral prosthesis 1100. FIG. 11C shows lateral view of the femoral prosthesis 1100. The femoral prosthesis 1100 includes many structures and features similar to those of the femoral prosthesis 900 described above. The femoral prosthesis 1100 is used in a hip replacement.

In one embodiment, the femoral prosthesis 1100 includes an implant body 1102 with a proximal end 1104, a distal end 1106, a medial column 1108, and a lateral column 1110.

In some embodiments, the implant body 1102 includes a long axis 1112 running through the center of the implant body 1102 along its length. The implant body 1102, in some embodiments, is substantially straight, and the long axis 1112 is substantially straight and in the center of the implant body 1102.

The implant body 1102 may include a medial column axis 1114. The medial column axis 1114 runs essentially through the center of the medial column 1108. The medial column axis 1114 may run through successive center points of the medial column 1108. In one embodiment, the medial column 1108 has a curved outer surface (best seen in FIG. 13) with a radius and a center point. In some embodiments, the medial column axis 1114 runs through the center points. In one embodiment, the medial column axis 1114 is substantially parallel to the long axis 1112.

The implant body 1102 may include a lateral column axis 1116. The lateral column axis 1116 runs essentially through the center of the lateral column 1110. The lateral column axis 1116 may run through successive center points of the lateral column 1110. In one embodiment, the lateral column 1110 has a curved outer surface (best seen in FIG. 13) with a radius and a center point. In some embodiments, the lateral column axis 1116 runs through the center points. In one embodiment, the lateral column axis 1116 is substantially parallel to the long axis 1112. In some embodiments, the medial column axis 1114 and the lateral column axis 1116 are substantially parallel.

As perhaps best observed in FIGS. 11A and 11C, terminal ends 1109 and 1111 of the medial column 1108 and lateral column 1110, respectively, may be C-shaped, each having a pair of free end portions or tips 1113 as shown in the FIGS. 11A and 11C. Thus, it will be understood that a cross-section of each of the medial column 1108 and the lateral column 111 may be C-shaped.

The implant body 1102, in some embodiments, includes a medial cannula 1118. The medial cannula 1118 may run the length of the implant body 1102 such that it is accessible at both the proximal end 1104 and the distal end 1106 of the implant body 1102. In one embodiment, the medial cannula 1118 runs along the medial column axis 1114. The medial cannula 1118 provides a pathway for a guide wire to guide the implant body 1102 during installation.

In some embodiments, the implant body 1102 includes a lateral cannula 1120. The lateral cannula 1120 may run the length of the implant body 1102 such that it is accessible at both the proximal end 1104 and the distal end 1106 of the implant body 1102. In one embodiment, the lateral cannula 1120 runs along the lateral column axis 1116. The lateral cannula 1120 provides a pathway for a guide wire to guide the implant body 1102 during installation.

The medial column 1108, in one embodiment, has an inside surface 1122. The inside surface 1122 may be formed, by a taper of the connecting body relative to the medial column 1108. In one embodiment, the inside surface 1122 is substantially concave over at least a portion of the inside surface 1122. The lateral column 1110 may have a corresponding inside surface (not shown) which may also be substantially concave over at least a portion of the inside surface of the lateral column 1110.

Figure 12:
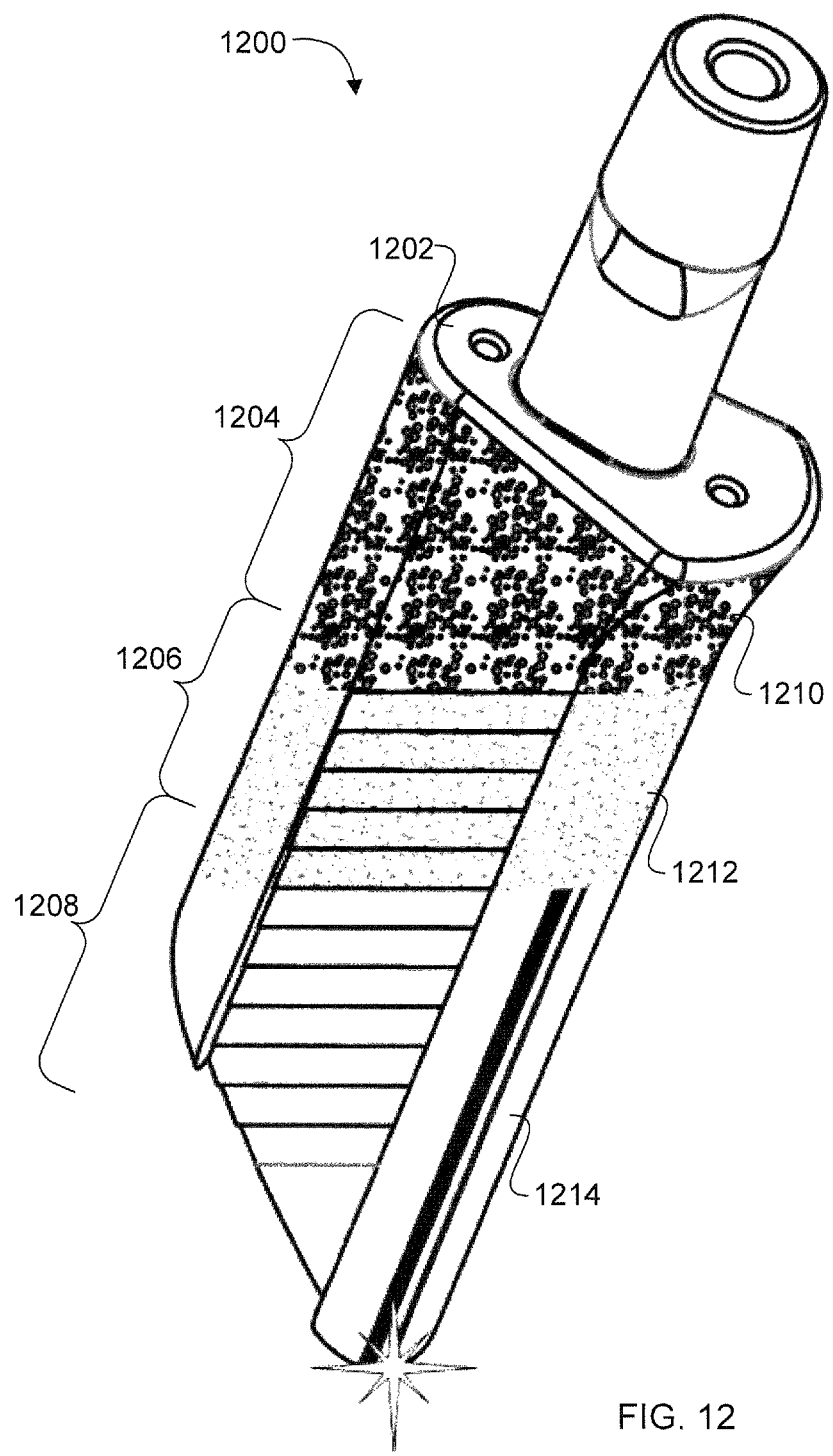
FIG. 12 illustrates an embodiment, of a hip prosthesis having a plurality of surface treatments.

FIG. 12 illustrates an embodiment of a hip prosthesis 1200 having a plurality of surface treatments. The hip prosthesis includes an implant body 1202 having a proximal region 1204, an intermediate region 1206, and a distal region 1208.

In some embodiments, the proximal region 1204 has a first surface treatment 1210 that is relatively porous. The relatively high porosity of the first surface treatment 1210 encourages bone ingrowth and acts to secure the proximal region 1204 of the implant body 1202 to the bone when the implant body 1202 is installed.

The intermediate region 1206, in one embodiment, has a second surface treatment 1212 that has an intermediate porosity. The intermediate porosity of the second surface treatment 1212 encourages some bone ingrowth, but less than that of the first surface treatment 1210. Consequently, bone ingrowth over the intermediate region 1206 secures the implant body 1202 to a degree, but less so than the proximal region 1204. The somewhat reduced fixation over the intermediate region 1206 may facilitate retrieval of the implant body 1202.

In one embodiment, the distal region 1208 has a third surface treatment 1214 having a low porosity. The low porosity of the third surface treatment 1214 resists bone ingrowth, resulting in relatively weaker fixation of the distal region 1208 to the femur. The weaker fixation of the distal region 1208 may facilitate retrieval of the implant body 1202.

In some embodiments, boundaries between the first surface treatment 1210, the second surface treatment 1212, and the third surface treatment 1214 are well defined. The boundaries may be angled relative to a long axis of the implant body 1202, or they may be perpendicular to the long axis of the implant body 1202. In one embodiment, the boundaries are angled such that they proceed in a lateral and distal direction, as shown in FIG. 12. In an alternate embodiment, the boundaries are angled such that they proceed in a medial and distal direction.

Figure 13:
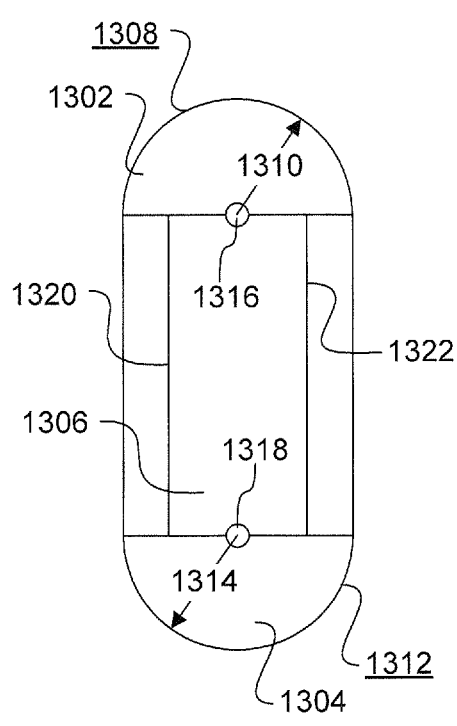
FIG. 13 depicts a lateral cross-sectional view of one embodiment of an implant body for a hip prosthesis.

FIG. 13 depicts a lateral cross-sectional view of one embodiment of an implant body for a hip prosthesis. The lateral cross-sectional view is taken along a plane perpendicular to a long axis of the implant body. The cross-sectional view shows a lateral column 1302, a medial column 1304, and a connecting body 1306.

The lateral column 1302, in one embodiment, includes a lateral outer surface 1308 that defines a portion of a perimeter of the implant body. The cross section of the lateral outer surface 1308 is substantially at least a portion of a circle, or an arc. In certain embodiments, the cross section of the lateral outer surface 1308 of the lateral column 1302 includes an arc having a constant radius 1310. In one embodiment, the lateral outer surface 1308 is a semicircle.

The medial column 1304, in one embodiment, includes a medial outer surface 1312 that defines a portion of a perimeter of the implant body. The cross section of the medial outer surface 1310 is substantially at least a portion of a circle, or an arc. In certain embodiments, the cross section of the medial outer surface 1312 of the medial column 1304 includes an arc having a constant radius 1314. In one embodiment, the medial outer surface 1312 is a semicircle.

In one embodiment, the radius 1310 of the lateral outer surface 1308 and the radius 1314 of the medial outer surface 1312 are substantially equal. In one embodiment, the cross-sectional area of the medial column 1304 is substantially equal to the cross-sectional area of the lateral column 1302.

The lateral column 1302, in some embodiments, includes a lateral cannula 1316 at the center point of the arc defining the lateral outer surface 1308. In one embodiment, the medial column 1304 includes a medial cannula 1318 at the center point of the arc defining the medial outer surface 1312.

In certain embodiments, the connecting body 1306 includes an anterior wall 1320 and a posterior wall 1322. The cross section of the anterior wall 1320 and the posterior wall 1322 area parallel in one embodiment.

Figure 14:
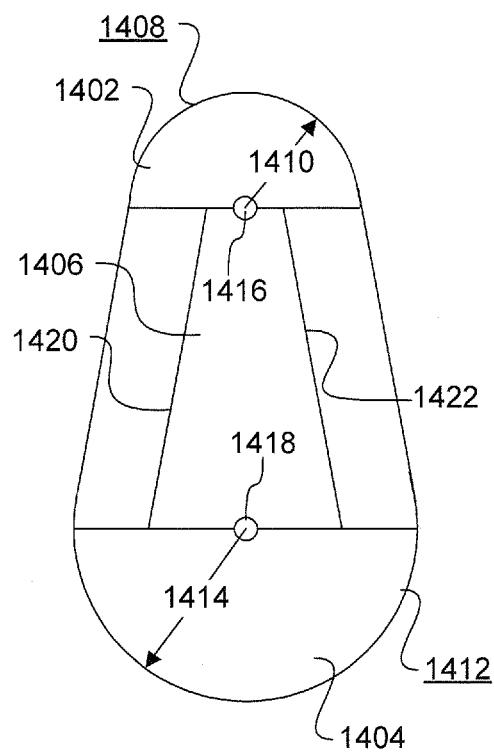
FIG. 14 depicts a lateral cross-sectional view of another embodiment of an implant body for a hip prosthesis.

FIG. 14 depicts a lateral cross-sectional view of one embodiment of an implant body for a hip prosthesis. The lateral cross-sectional view is taken along a plane perpendicular to a long axis of the implant body. The cross-sectional view shows a lateral column 1402, a medial column 1404, and a connecting body 1406.

The lateral column 1402, in one embodiment, includes a lateral outer surface 1408 that defines a portion of a perimeter of the implant body. The cross section of the lateral outer surface 1408 is substantially at least a portion of a circle, or an arc. In certain embodiments, the cross section of the lateral outer surface 1408 of the lateral column 1402 includes an arc having a constant radius 1410. In one embodiment, the lateral outer surface 1408 is a semicircle.

The medial column 1404, in one embodiment, includes a medial outer surface 1412 that defines a portion of a perimeter of the implant body. The cross section of the medial outer surface 1410 is substantially at least a portion of a circle, or an arc. In certain embodiments, the cross section of the medial outer surface 1412 of the medial column 1404 includes an arc having a constant radius 1414. In one embodiment, the medial outer surface 1412 is a semicircle.

In one embodiment, the radius 1410 of the lateral outer-surface 1408 and the radius 1414 of the medial outer surface 1412 are substantially different. For example, the radius 1414 of the medial outer surface 1412 may be larger than the radius 1410 of the lateral outer surface 1408. In one embodiment, the cross-sectional area of the medial column 1404 is thirty (30) percent larger than the cross-sectional area of the lateral column 1402.

In certain embodiments, the connecting body 1406 includes an anterior wall 1420 and a posterior wall 1422. The cross section of the anterior wall 1420 and the posterior wall 1422 are angled relative to one another in one embodiment.

The lateral column 1402, in some embodiments, includes a lateral cannula 1416 at the center point of the arc defining the lateral outer surface 1408. In one embodiment, the medial column 1404 includes a medial cannula 1418 at the center point of the arc defining the medial outer surface 1412.

Figure 15:
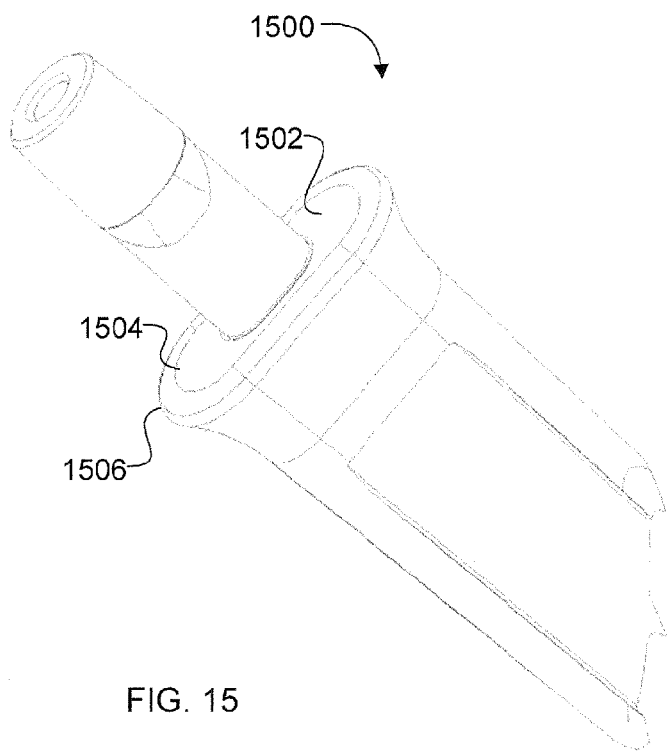
FIG. 15 is a perspective view illustrating one embodiment of a femoral prosthesis.

FIG. 15 is a perspective view illustrating one embodiment of a femoral prosthesis 1500. The femoral prosthesis includes an implant body 1502. The femoral prosthesis 1500 is used in hip replacement.

The implant body 1502, in one embodiment, includes a proximal end 1504 with a collar 1506 disposed at or near the proximal end 1504. The collar 1506 may be a portion of the implant body 1502 that extends radially as the proximal end 1504 of the implant body 1502 is approached along the implant body 1502. The collar 1506 may serve to limit the extent to which the implant body 1502 may be inserted into the femur. As illustrated in FIG. 15, the implant body 1502 may include a collar 1506. In an alternate embodiment, the implant body 1502 may be collarless.

Figure 16:
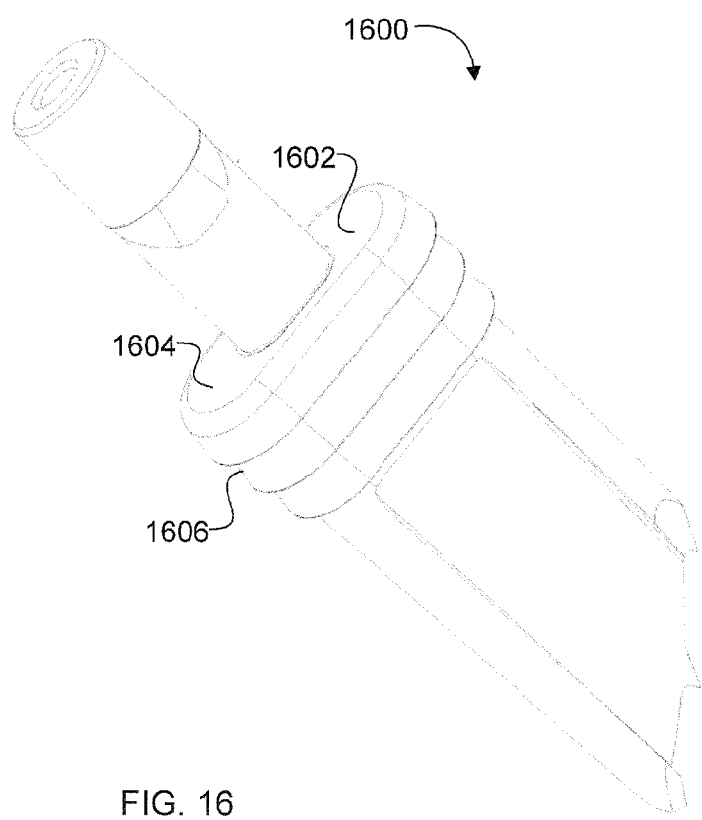
FIG. 16 is a perspective view illustrating another embodiment of a femoral prosthesis.

FIG. 16 is a perspective view illustrating one embodiment of a femoral prosthesis 1600. The femoral prosthesis includes an implant body 1602. The femoral prosthesis 1600 is used in hip replacement.

The implant body 1602, in one embodiment, includes a proximal end 1604 with a stepped shoulder 1606 disposed at or near the proximal end 1604. The stepped shoulder 1606 may be a portion of the implant body 1602 that includes one or more steps. The stepped shoulder 1606 may serve to improve bone ingrowth and fixation of the implant body 1602 within the femur. As illustrated in FIG. 16, the implant body 1602 may include a stepped shoulder 1606. In an alternate embodiment, the implant body 1602 may be have a smooth shoulder.

Figure 17A:
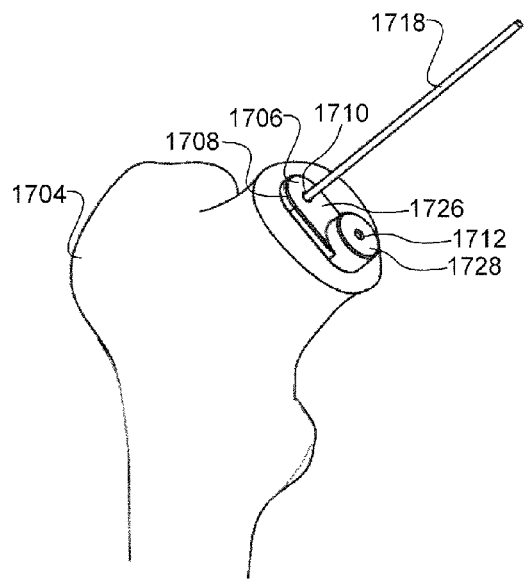
FIGS. 17A-17F illustrate one embodiment of a system and method for installing a hip implant body into a femur.
Figure 17B:
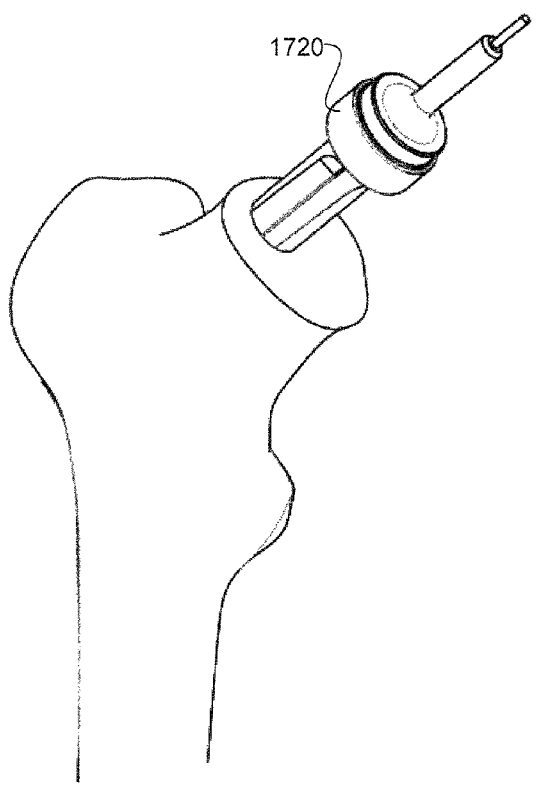

FIGS. 17A-17F illustrate one embodiment of a system and method for installing a hip implant body 1702 into a femur 1700. As shown in FIG. 17A, a neck sizing template 1706 may be positioned on a resected neck of the femur 1704. The neck sizing template 1706 may be of a size selected to match the size of the femur 1704. For example, the femur 1704 may have a relatively large neck, and a correspondingly relatively large neck sizing template 1706 may be selected for positioning on the resected neck of the femur 1704.

The neck sizing template 1706, in one embodiment, has an outer perimeter 1708 similar to the outer perimeter of the implant body 1702. For example, the neck sizing template 1706 may have an outer perimeter 1708 that is roughly equal to that of the implant body 1702. A neck sizing template 1708 similar in size to the implant body 1702 provides a tool for visualizing and testing the size of the implant body 1702 relative to the neck of the femur 1704.

In another embodiment, the neck sizing template 1706 is undersized relative to the implant body 1702, having an outer perimeter 1708 less than the outer perimeter of the implant body 1702. A neck sizing template 1708 having an outer perimeter 1708 smaller than that of the implant body 1702 may result in an undersized channel in the femur 1704, and a tighter fit for the implant body 1702.

The neck sizing template 1706, in one embodiment, includes a first aperture 1710 and a second aperture 1712. The first and second apertures 1710, 1712 may correspond to and be alignable with a medial cannula 1714 and a lateral cannula 1716 of the implant body 1702. The neck sizing template 1706 may be positioned such that one of the first aperture 1710 and the second aperture 1712 is positioned laterally from the center of the resected neck of the femur 1704 and so that the other of the first aperture 1710 and the second aperture 1712 is positioned medially from the center of the resected neck of the femur 1704.

In some embodiments, a first guide wire 1718 is inserted through the first aperture 1710 and into the femur 1704. The neck sizing template 1706 may guide and direct the first guide wire 1718 in a particular direction and orientation as it is inserted into the femur 1704.

The first guide wire 1718 may be inserted into the femur 1704 using any technique. For example, the first guide wire 1718 may be driven into the femur 1704 using a power drill. In another example, the first guide wire 1718 may be impacted into the femur 1704.

Subsequent to the first guide wire 1718 being inserted into the femur 1704, the neck sizing template 1706 may be removed from the femur 1704 and the first guide wire 1718. With the first guide wire 1718 inserted into the femur 1704, a cannulated tool 1720 may be positioned over the first guide wire 1718. The cannulated tool 1720 may be used to form a first channel 1722 in the femur 1704 in preparation for installation of the implant body 1702. The cannulated tool 1720 may follow the first guide wire 1718 and form the first channel 1722 around the first guide wire 1718. For example, the cannulated tool 1720 may be a cannulated reamer, and the cannulated reamer may ream a channel around the first guide wire 1718.

The neck sizing template 1708 may have a first surface 1724 and a second surface 1726. The first and second apertures 1710, 1712 may each run perpendicular to and through the first surface 1724 and the second surface 1726. In one embodiment, the first surface 1724 is substantially planar or flat. The flat first surface 1724 is beneficial for stable placement of the neck sizing template 1708 on the resected neck of the femur 1704.

In some embodiments, the second surface 1726 has a positioning plug 1728 to extend into the first channel 1722 formed around the first guide wire 1718. The positioning plug 1728 may be placed over the first guide wire 1718 and stabilized within the first channel 1722. The positioning plug 1728 may stabilize the neck sizing template 1708 to position one of the first aperture 1710 and the second aperture 1712 relative to the first guide wire 1718, with the other of the first aperture 1710 and the second aperture 1712 passing through the positioning plug 1728. The first guide wire 1718 may be position through the positioning plug 1728 via one of the first aperture 1710 and the second aperture 1712.

Figure 17C:
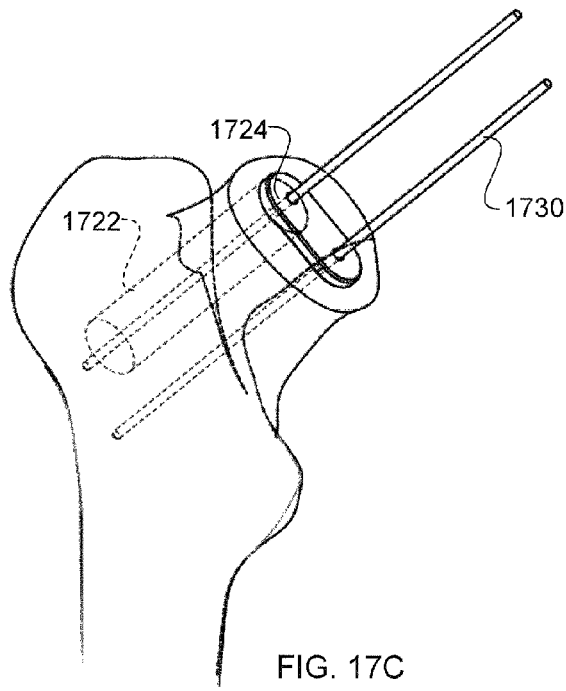
Figure 17D:
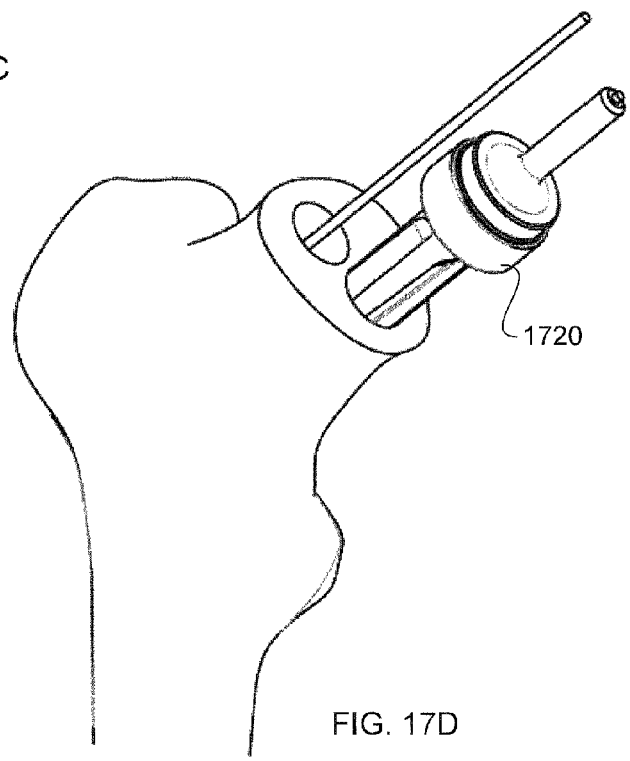
Figure 17E:
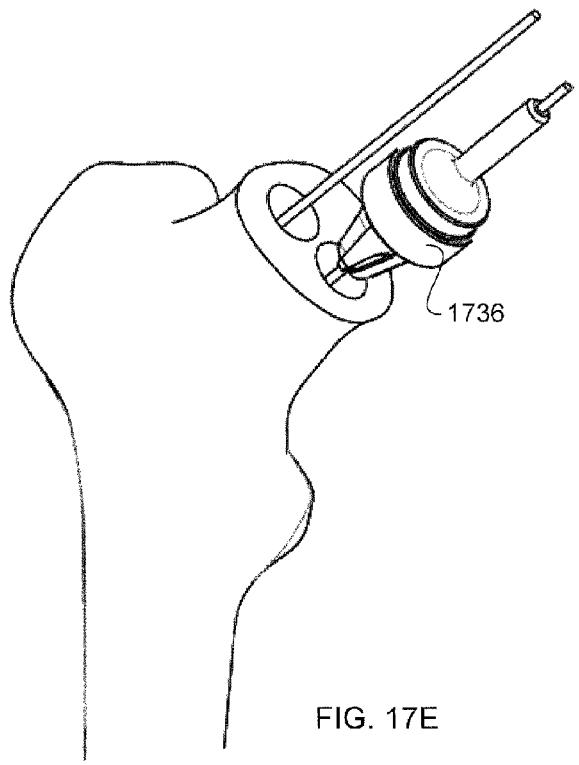

As shown in FIG. 17C, a second guide wire 1730 may be inserted through the one of the first aperture 1710 and the second aperture 1712 and into the femur 1704. The neck sizing template 1706 may guide and direct the second guide wire 1730 in a particular direction and orientation as it is inserted into the femur 1704. The neck sizing template 1706 may be positioned at least in part by one of the first guide wire 1718 and the positioning plug 1728. The second guide wire 1730 may be substantially parallel to the first guide wire 1718.

The second guide wire 1730 may be inserted into the femur 1704 using any technique. For example, the second guide wire 1730 may be driven into the femur 1704 using a power drill. In another example, the second guide wire 1730 may be impacted into the femur 1704.

Subsequent to the second guide wire 1730 being inserted into the femur 1704, the neck sizing template 1706 may be removed from the femur 1704 and the second guide wire 1730. With the second guide wire 1730 inserted into the femur 1704, a cannulated tool 1720 may be positioned over the second guide wire 1730. The cannulated tool 1720 may be used to form a second channel 1732 in the femur 1704 in preparation for installation of the implant body 1702. The cannulated tool 1720 may follow the second guide wire 1730 and form the second channel 1732 around the first guide wire 1718. For example, the cannulated tool 1720 may be a cannulated reamer, and the cannulated reamer may ream a channel around the second guide wire 1730.

In some embodiments, the cannulated tool 1720 used to form the second channel 1732 has the same diameter of the cannulated tool 1720 used to form the first channel 1722. In an alternate embodiment, the second channel 1732 is formed using a different cannulated tool than that used to form the first channel 1722. For example, the implant body 1702 may have substantially different sized medial and lateral columns, and the first and second channels may be formed to correspond to these sizes using different sized cannulated tools.

In certain embodiments, the implant body 1702 may have a flare 1734 along a proximal portion of the implant body 1702. An additional cannulated tool 1736 may be used to expand a channel 1722, 1732 to accommodate the flare 1734. For example, the flare 1734 may be at least partially conical, and the additional cannulated tool 1736 may be a cannulated conical reamer.

Figure 17F:
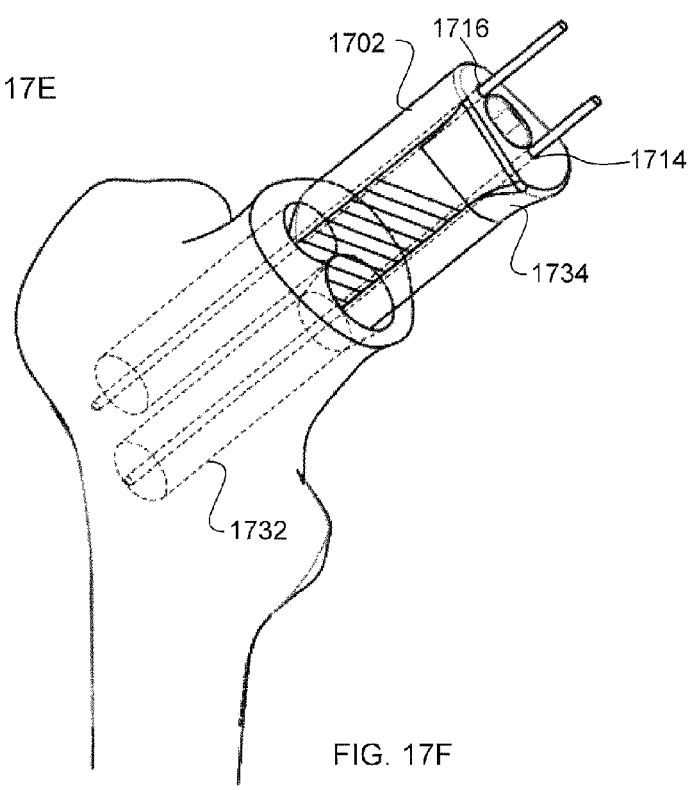

As shown in FIG. 17F, the implant body 1702 may be positioned with the first and second guide wires 1718, 1730 running through the medial and lateral cannulas 1714, 1716, one guide wire per cannula. The implant body 1702 may progress long the guide wires 1718, 1730 and into the first and second channels 1722, 1732. The implant body 1702 may be pressed into the femur 1704 using any technique for pressing an implant body 1702 into a femur 1704. For example, the implant body 1702 may be driven into the femur 1704 using a hammer. The guide wires 1718, 1730 may guide the implant body 1702 into a desired position within the femur 1704.

Those having ordinary skill in the relevant art will appreciate the advantages provide by the features of the present disclosure. In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A femoral prosthesis comprising:
an implant body having a proximal end and a distal end, the proximal end being dimensioned and configured to support a prosthetic neck, a majority of the implant body further comprising a trunk comprising:
a medial column extending toward the distal end on a medial side of the implant body;
a lateral column extending toward the distal end on a lateral side of the implant body; and
a connecting body disposed between the medial column and the lateral column, where the medial column and the lateral column of the implant body are spaced apart, the connecting body tapering from the proximal to the distal end of the implant body and tapering from the lateral column to the medial column;
wherein a terminal end of at least one of the medial column and the lateral column is C-shaped, each having a pair of free end portions, a convex outer surface and a concave inner surface, wherein the connecting body extends from a central portion of the concave surface.

2. The femoral prosthesis of claim 1, wherein the connecting body is thinner than, and intercouples, the medial column and the lateral column.

3. The femoral prosthesis of claim 2:
wherein the implant body further comprises a shoulder at the proximal end, the shoulder being structured and dimensioned for a tight press fit into a neck of a femur;
wherein the connecting body comprises a wedge formed by a tapered portion extending in the direction of the distal end of the implant body;
wherein the wedge, the medial column, and the lateral column are configured and arranged to provide multi-planar stability for the implant body and fixation of the implant body with the femur.

4. The femoral prosthesis of claim 1, wherein the medial column is wider than the lateral column at the proximal end of the implant body.

5. A femoral prosthesis comprising:
an implant body having a proximal end and a distal end, the proximal end being dimensioned and configured to support a prosthetic neck, the implant body comprising:
a shoulder at the proximal end, the shoulder being structured and dimensioned for a tight press fit into a neck of a femur; and
a trunk at the distal end, the trunk comprising:
a wedge formed by a tapered portion extending in the direction of the distal end of the implant body;
a medial column extending from the shoulder toward the distal end, the medial fin disposed on a medial side of the wedge; and
a lateral column extending from the shoulder toward the distal end, the lateral fin disposed on a lateral side of the wedge;
wherein the wedge, the medial column, and the lateral column are configured to provide multi-planar stability for the implant body and fixation of the implant body with the femur;
wherein a terminal end of at least one of the medial column and the lateral column is C-shaped, each having a pair of free end portions, a convex outer surface and a concave inner surface, wherein the connecting body extends from a central portion of the concave surface;
wherein the medial column is wider than the lateral column at the shoulder.

6. The femoral prosthesis of claim 5, wherein the implant body has an elongated lateral cross-section.

7. The femoral prosthesis of claim 5, wherein the implant body has a substantially straight long axis so that the implant body does not curve into the diaphysis of the femur.

8. The femoral prosthesis of claim 5, wherein the medial column has a substantially straight long axis.

9. The femoral prosthesis of claim 5, wherein the distal end of the implant body is generally angled relative to a long axis of the implant body, so that the distal end, when inserted into the femur, is generally parallel to a longitudinal axis of the femur.

10. The femoral prosthesis of claim 9, wherein a curved surface is superimposed on the angled distal end of the implant body so that the distal end of the implant body is curved transversely in relation to the long axis of the implant body.

11. The femoral prosthesis of claim 5, wherein the medial column is substantially the same size as the lateral column by cross-sectional area.

12. The femoral prosthesis of claim 5, wherein an inner surface of at least one of the lateral and the medial column is concave.

13. The femoral prosthesis of claim 5, wherein the wedge begins at a portion of the implant body located in the cancellous region of the femur when the implant body is installed.

14. The femoral prosthesis of claim 5, wherein the wedge comprises an anterior wall and a posterior wall, and wherein the anterior wall and the posterior wall are substantially parallel in lateral cross-section.

15. The femoral prosthesis of claim 5, wherein the implant body is sized so that the distal end of the implant body extends a length of between sixty (60) percent and eighty (80) percent of a distance from a resection of a femur head of a femur to an inner cortical lateral wall of the femur.

16. The femoral prosthesis of claim 5, wherein the trunk tapers from the proximal to the distal end of the implant body and tapers from the lateral column to the medial column.

* * * * *